(12) United States Patent
Faatz et al.

(10) Patent No.: US 6,489,129 B1
(45) Date of Patent: Dec. 3, 2002

(54) ANTIGEN-SPECIFIC IGM DETECTION

(75) Inventors: Elke Faatz, Huglfing (DE); Urban Schmitt, Oberhausen (DE); Beatus Ofenloch-Hahnle, Polling (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/319,084

(22) PCT Filed: Nov. 26, 1997

(86) PCT No.: PCT/EP97/06583

§ 371 (c)(1),
(2), (4) Date: Nov. 15, 1999

(87) PCT Pub. No.: WO98/23955

PCT Pub. Date: Jun. 4, 1998

(30) Foreign Application Priority Data

Nov. 29, 1996 (DE) .......................... 196 49 389

(51) Int. Cl.⁷ .............................. G01N 33/53
(52) U.S. Cl. .................. 435/7.5; 435/7.1; 435/7.9; 435/7.92; 435/7.94; 435/962; 436/507; 436/509; 436/512; 436/513; 436/518; 436/825
(58) Field of Search ................... 435/7.1, 7.5, 7.9, 435/7.92, 7.94, 962; 436/507, 509, 512, 513, 518, 825

(56) References Cited

U.S. PATENT DOCUMENTS 5,670,309 A * 9/1997 Norrby et al.
5,804,371 A * 9/1998 Hoss et al.
5,804,391 A * 9/1998 Klemt et al.
5,965,378 A * 10/1999 Schlieper et al.

FOREIGN PATENT DOCUMENTS

| DE | 44 39 452 A2 | * 5/1996 | |
|---|---|---|---|
| WO | WO 96/03652 | 2/1996 | |
| WO | WO 96/14337 | 5/1996 | ........... C07K/16/00 |
| WO | WO 96/14338 | 5/1996 | ........... C07K/16/00 |

OTHER PUBLICATIONS

Lee, et al., "The Influence of Beta–Alanine and 4–Aminobutyric Acid Residues on the Solubility of Peptides Containing Them," Bull. Chem. Soc. Jpn. 66:2006–2010 (1993).

* cited by examiner

*Primary Examiner*—Bao-Thuy L. Nguyen
(74) *Attorney, Agent, or Firm*—Marilyn L. Amick; Roche Diagnostics Corporation

(57) ABSTRACT

The invention concerns a method for the determination of antigen-specific antibodies of the immunoglobulin M class in the presence of immunoglobulins of the G class and/or rheumatoid factors in body fluids by incubation with at least two different receptors $R_1$ and $R_2$ and optionally additional receptors wherein an essential component of $R_2$ is a binding partner in a polymeric form and interference by IgG antibodies of the same antigen specificity is reduced by binding partners in a monomeric form; a reagent for determining an antigen-specific antibody of the immunoglobulin M class, as well as the use of binding partners in a monomeric form to reduce interference by IgG antibodies in the determination of antigen-specific IgM antibodies.

8 Claims, No Drawings

ANTIGEN-SPECIFIC IGM DETECTION

The invention concerns a method for the determination of antigen-specific antibodies of the immunoglobulin M class in body fluids by incubating the sample with at least two different receptors $R_1$ and $R_2$ where both receptors are capable of binding specifically to the antibody, $R_1$ is bound or can be bound to a solid phase and $R_2$ carries a label, wherein an essential component of $R_1$ and optionally also of $R_2$ is a binding partner in polymeric form which is specifically recognized by the antibody to be determined and binding partners of the same specificity are used in monomeric form to reduce interference by IgG antibodies.

In particular the invention concerns a method for the specific detection of immunoglobulins of the IgM class in the presence of immunoglobulins of the IgG class and interfering factors such as rheumatoid factors.

In response to the introduction of foreign substances the immune system of a mammalian organism produces antibodies which are also called immunoglobulins. They defend against foreign substances which are also referred to as antigens. The immunoglobulins can be divided into five different classes. One distinguishes between immunoglobulins of the M, G, A, E and D classes. Each of these five immunoglobulin classes differ in the composition of the heavy chain which is referred to as the $\mu$, $\gamma$, $\alpha$, $\epsilon$ and $\delta$ chain.

Each immunoglobulin class has a different function in the organism. Immunoglobulins of the M class appear after the first contact with the antigen, the so-called primary immunization. However, the concentration of these immunoglobulins decreases rapidly as the infection progresses. The immunoglobulins of the G class are firstly slowly formed after a primary immunization and occur in large quantities when there is a second infection with the same antigen. The immunoglobulins of the A class are found on the mucous membrane surfaces of the organism and are responsible for the defence processes there. The immunoglobulins of the E class are mainly responsible for allergic reactions. The exact function of immunoglobulins of the D class is hitherto unknown.

The individual immunoglobulin classes occur in very different concentrations in the blood. Thus immunoglobulins of the G class (IgG) are the major class in normal human serum with a share of about 75% that corresponds to a serum content of 8 to 18 mg/ml. The second most frequently occurring immunoglobulin is IgA which has an average serum concentration of 0.9 to 4.5 mg/ml. Immunoglobulins of the M class are present at a concentration of 0.6 to 2.8 mg/ml, immunoglobulins of the D class are present at a concentration of 0.003 to 0.4 mg/ml. The proportion of IgE antibodies is lowest and they only occur at a concentration of 0.02 to 0.05 $\mu$g/ml in serum.

For the differential diagnosis of many diseases it is important to detect antibodies of one or several quite particular immunoglobulin classes which are specific for a particular antigen. A satisfactory diagnosis of viral, bacterial and parasitic infections can only be ensured by means of a class-specific antibody test or by excluding the presence of certain immunoglobulin classes (e.g. detection of IgG and IgA antibodies but no detection of IgM antibodies). This is particularly important for distinguishing between fresh or acute infections and infections that have occurred earlier as well as for the clinical monitoring of the course of an infection. The class-specific detection of antibodies is especially important for HIV, hepatitis A, hepatitis B, toxoplasmosis, rubella and chlamydia infections. The class-specific detection of antibodies specific for a particular antigen is also necessary when determining the titre of protecting antibodies and to check the success of an immunization. For the diagnosis of fresh, acute infections it is of particular interest to detect antibodies of the IgM class which are specific for an antigen. However, various interfering factors such as for example the presence of IgG antibodies of the same specificity frequently interfere with the detection of antigen-specific IgM antibodies.

Various methods have been described in the state of the art for detecting antibodies of a particular class that are specific for an antigen. Hence antigen-specific antibodies of a particular class are frequently detected by binding the specific antibodies to a solid phase coated with the specific antigen. The immunoglobulins (Ig) specific for the antigen which are now bound to the solid phase are detected by binding antibodies which are specifically directed towards human Ig of a certain class to the Ig molecules to be detected. The antibodies directed towards human Ig are provided with a label by means of which the detection takes place. However, such a test procedure is only possible if all unspecific non-bound Ig is removed by washing before the reaction with the class-specific labelled antibodies directed towards human Ig. Thus a one-step test procedure as is often required for automated systems is not possible. In addition antibodies of all classes which are specific for the antigen bind to the solid phase in the first step. If the antigen coating of the solid phase is not high enough, competing reactions of the various antibody classes for binding to the antigen can occur. This can impair the sensitivity of the test.

One possibility of carrying out an antibody detection in a one-step test is provided by the so-called bridge test. The bridge test concept is described in EP-A-0 280 211. In this method a first receptor such as for example an antigen which is capable of specific binding to the antibody to be determined is bound to a solid phase. The antibody to be determined binds to the solid phase-bound antigen. In addition a further specific antigen is present in the test mixture which is provided with a label. The antibody is detected by means of the label. However, in this test all antigen-specific antibodies are detected and not only the antibodies of a particular class.

An additional interference when determining antigen-specific IgM antibodies is caused by rheumatoid factors. Rheumatoid factors are themselves usually antibodies of the IgM class which generally have a high affinity for the Fc regions of IgG antibodies. As a result rheumatoid factors seemingly present IgG antibodies so that the rheumatoid factors are bound in an immunoassay for specific IgM antibodies. If the rheumatoid factors have bound IgG molecules with the specificity that is to be detected, this can result in false-positive measurement results.

This problem in the class-specific detection of antigen-specific antibodies is the subject matter of DE 33 03 793. This describes a method for the detection. of an antigen-specific antibody of a certain Ig class ("IgX") in which interference by rheumatoid factors is eliminated by adding anti-IgG antibodies. In the method the specific antigen, such as a virus antigen, is applied to a solid carrier. The virus antigen bound to the solid phase is contacted with the sample. In the next step the unbound sample is removed and the solid phase-bound complex of antigen-IgX is detected with an anti-IgX antibody. In order to avoid interference by rheumatoid factors especially in IgM tests, the sample is treated with anti-IgG antibodies before the test. The IgG antibodies complexed in this manner are thus no longer available for attack by rheumatoid factors so that the rheumatoid factors are not able to bind antigen-specific IgG molecules which could in turn result in false-positive results. However, all IgG antibodies are bound regardless of their specificity. The precipitation of interfering IgG antibodies with anti-IgG antibodies can lead to undesired precipitates and turbidity which can have an adverse effect on the entire test. In addition sample pretreatment with anti-IgG antibodies is complicated.

A further method of eliminating interference by antibodies of other classes with the same specificity is disclosed in WO 96/14337. In this case antibodies or antibody fragments which react specifically with the Fd section of the heavy chain of IgG are used to eliminate interference by IgG antibodies. As a result the antigen binding capability of the IgGs is masked so strongly that they are no longer able to recognize the specific antigens. A similar concept is described in WO 96/14338.

In this case anti-Fd antibodies or fragments thereof are used as an interference-eliminating reagent to reduce interference by rheumatoid factors. However, reduction of interference by a highly specific anti-Fd reagent is complicated and costly.

The methods known in the prior art do not enable detection of an antigen-specific antibody of the immunoglobulin IgM class in a one-step method without having to add elaborate and expensive interference-eliminating reagents and/or several specific antibodies. The immunological methods of detection known from the state of the art based on the bridge test concept in which a labelled antigen and an antigen capable of binding to a solid phase are used, do indeed enable a one-step test. However, up to now it has only been possible to jointly detect antibodies of the IgG and IgM classes using this simple principle.

Therefore the object was to provide an improved method for the detection of antibodies of the IgM class directed against a specific antigen. This method should not require elaborate and expensive interference-eliminating reagents and should preferably consist of a one-step test principle in order to be used advantageously in automated systems.

This object is achieved by the method according to the invention for the determination of an antigen-specific antibody of the immunoglobulin M class by incubating the sample with at least two different receptors $R_1$ and $R_2$ where both receptors are capable of binding specifically to the antibody, $R_1$ is bound or can be bound to a solid phase and $R_2$ carries a label, wherein an essential component of $R_1$ is a binding partner in polymeric form which is specifically recognized by the antibody to be determined, and interference by IgG molecules of the same specificity present in the sample is eliminated by adding binding partners in monomeric form.

The IgA, IgD and IgE antibodies present in the sample which have the same specificity as the IgM antibodies to be detected occur in very low concentrations compared to IgG antibodies so that no interference by the classes IgA, IgD and IgE would be expected. The antibody classes IgA, IgD and IgE are—like IgG molecules and in contrast to the IgM antibodies that are present as a pentamer—antibodies which are present in the form of single molecules and each has two binding sites for the antigen. Hence due to the structural similarity of IgG, IgA, IgD and IgE antibodies, interference by IgD, IgA and IgE antibodies is also presumably reduced in addition to that caused by IgG antibodies by the method for antigen-specific IgM detection described in the following.

The method according to the invention allows the determination of antigen-specific antibodies of the immunoglobulin M class in samples in which antibodies of the IgG class with the same antigen specificity are present. In addition the method according to the invention can be carried out in the presence of rheumatoid factors. An elaborate pretreatment of the sample is not necessary.

It has surprisingly turned out that the use according to the invention of binding partners in a monomeric form in an immunoassay for the detection of antigen-specific IgM antibodies enables an effective elimination of interference caused by IgG antibodies with the same antigen-specificity. In this method the binding partners in a monomeric form bind specifically to the antigen binding sites of the IgG antibodies. The IgM antibodies to be detected with the same specificity which are present in the same sample surprisingly do not react or only to a negligibly weak extent with the binding partners in a monomeric form. The term "negligibly weak" means that the antigen binding sites of the IgM antibodies are not blocked by the binding partners in monomeric form. This is presumably due to the much lower affinity of the pentameric IgM antibodies for monomeric epitopes compared to the IgG antibodies present in the form of individual molecules which have a substantially higher affinity for monomeric epitopes. This means that despite the presence of binding partners in a monomeric form, the sensitivity of the IgM test is not impaired. The IgG antibodies masked by the binding partners in a monomeric form do not interfere with the IgM test.

It has also surprisingly turned out that interference by rheumatoid factors that have bound IgG antibodies can also be effectively eliminated by the binding partners in monomeric form which bind to the antigen binding sites of the IgGs. Since the antigen binding sites of the IgG antibodies are blocked, the antigen-specific IgM antibodies can be detected without prior separation of the IgG antibodies or the rheumatoid factors. The binding partners used in monomeric form are not able to trigger an agglutination reaction of the masked IgG antibodies or the rheumatoid factors. This prevents undesired turbidities due to precipitates which can adversely influence the entire test procedure.

Hence a successive test procedure for separating the IgG antibodies is not absolutely necessary in the method according to the invention since these do not interfere. A particular advantage of the method is therefore the simplicity of the test procedure.

Apart from the so-called wet tests in which the test reagents are present in a liquid phase, all standard dry test formats which are suitable for the detection of proteins or antibodies can also be used. In these dry tests or test strips as described for example in EP-A-0 186 799, the test components are applied to a carrier. Hence if the method according to the invention is carried out in a test strip format no wash step is necessary. However, the method according to the invention is preferably carried out as a wet test.

It is possible to incubate all receptors and the binding partners in a monomeric form together with the sample and to carry out the method in one step. This optionally requires only one wash step after the incubation.

Normally two different receptors $R_1$ and $R_2$ and the binding partners in a monomeric form are used to carry out the method according to the invention. If a wet test is used, the receptor $R_2$ is present in a liquid phase. $R_1$ can be present in a liquid phase or already bound to the solid phase. The binding partners in a monomeric form are preferably present in the liquid phase.

If a receptor capable of binding to a solid phase but which is not yet bound to the solid phase is used as $R_1$ the sample is then incubated together with the receptors $R_1$ and $R_2$ and the binding partners in a monomeric form.

In this process the sample antibody binds to $R_1$ and $R_2$. This incubation can occur in the presence of the solid phase. A complex is formed in this process composed of solid-phase-$R_1$-sample antibody-$R_2$. Subsequently the solid phase is separated from the liquid phase, the solid phase is optionally washed and the label of $R_2$ is measured. The label is usually measured in the solid phase but it can also be determined in the liquid phase.

If the incubation of the sample with $R_1$ and $R_2$ and the binding partners in a monomeric form is carried out in the absence of the solid phase, then the entire test mixture must subsequently be contacted with the solid phase, the washing is optionally carried out and the label measured.

If the receptor $R_1$ is already in a solid phase-bound form, then the sample and receptor $R_2$ are added to the solid phase-bound receptor $R_1$ and incubated together. In this test procedure the sample is preferably preincubated with the binding partners in a monomeric form and $R_2$ before the test mixture is added to the solid phase-bound receptor $R_1$. The further procedure corresponds to the method stated above.

It is also possible to carry out the method according to the invention in several steps. In this case the sample is preferably incubated with the binding partners in a monomeric form and then with the receptors $R_1$ and $R_2$. The test mixture can subsequently be incubated with other receptors whereby this can be carried out in several steps. The further test procedure corresponds to the previously described method.

An important component of $R_1$ is a binding partner in a polymeric form which is specifically recognized by the IgM antibodies to be determined which can also be referred to as a polyhapten. A binding partner in a polymeric form according to the invention is understood as structures in which several, preferably identical or similar, equivalent epitope regions are coupled to a carrier which react specifically with the antibody to be determined. The term "similar" or "equivalent" means that the structures present on the binding partner in a polymeric form do not necessarily all have to be identical. The only condition is that the IgM antibodies to be determined bind specifically to these epitope regions. The epitope region can for example be derived from an antigen or anti-idiotype antibody. The epitope region can also be derived from sugar chains like those which for example occur in glycated proteins. It can also be derived from lipid structures like those which for example occur in phospholipids or lipoproteins. Hence the polyhapten or the binding partner in a polymeric form is composed of many identical or similar epitope regions and thus has many similar binding sites for the sample antibody as already set forth above. A binding site in the case of a protein as an antigen is understood as a peptide the sequence of which is a part of the protein sequence of a protein antigen (analyte) and to which an antibody specifically binds which is directed against this protein. In the case of an antigen which contains a sugar structure, the binding site would be the region of sugar molecules to which the sample antibody specifically binds. In the case of lipid structures, the lipid molecules can be the binding site for the sample antibody. A binding site can also be composed of combinations of peptidic regions with sugars and/or lipids. However, polyhaptens based on peptides are preferably used as binding partners in a polymeric form. In the case of the binding partners in a polymeric form according to the invention a high epitope density is of primary importance so that the pentameric IgM sample antibodies are able to specifically bind with high affinity to the binding partners in a polymeric form. The other criteria for the individual peptide components of the binding partners according to the invention in a polymeric form correspond to the requirements described below for the binding partners in a monomeric form.

Particles of for example latex, polystyrene, polyacrylate, polymethacrylate or gold can be used as the carrier material for the polyhaptens. Polymers such as dextran or polypeptides such as polylysine, bovine serum albumin, β-galactosidase, unspecific immunoglobulins or fragments thereof can also be used as a carrier material for the polyhaptens. The only condition in selecting the carrier is that it has no cross-reactivity with antibodies in the sample liquid. A further condition is that it must be possible to couple the haptens to the carrier. The epitope regions or haptens are coupled to the carrier material by methods known to a person skilled in the art as described for example in EP-A-0 650 053 and WO 96/03652. In addition spacer regions can be inserted between the epitope region and carrier material which are also described in the aforementioned unexamined laid-open patent application. All spacer regions known to a person skilled in the art can be used. A requirement is that they are immunologically inactive i.e. they do not cross-react with antibodies in the sample.

$R_1$ can either be bound directly to the solid phase or it is bound indirectly to the solid phase by means of a specific binding system. The direct binding of $R_1$ to the solid phase is achieved by methods known to a person skilled in the art. If $R_1$ is indirectly bound to the solid phase by means of a specific binding system, then $R_1$ is a conjugate which is composed of a binding partner according to the invention in a polymeric form and a reaction partner of a specific binding system. A specific binding system is in this case understood as two partners which can react specifically with one another. In this case the binding capability can be based on an immunological reaction or on another specific reaction. A combination of biotin and avidin or biotin and streptavidin is preferably used as a specific binding system. Other preferred combinations are biotin and antibiotin, hapten and anti-hapten, Fc fragment of an antibody and antibody against this Fc fragment or carbohydrate and lectin. One of the reaction partners of this specifically bindable pair is then a part of the conjugate that forms the receptor $R_1$.

The other reaction partner of the specific binding system is then present in a solid phase. The other reaction partner of the specific binding system can be bound to an insoluble carrier material by conventional methods known to a person skilled in the art. In this case a covalent as well as an adsorptive binding is suitable. Solid phases that are particularly suitable are test tubes or microtitre plates made of polystyrene or similar plastics the inner surfaces of which are coated with the reaction partner of the specific binding system. Particulate substances such as latex particles, molecular sieve materials, glass beads, plastic tubes etc. are also suitable and particularly preferred. Porous layered carriers such as paper can also be used as the carrier.

The receptor $R_2$ is composed of a molecule which reacts specifically with the sample antibody and a label. The molecule that reacts specifically with the sample antibody can for example be an antibody, an antibody fragment, a protein, an antigen or a hapten which bind specifically to the sample antibody. The only condition for the molecule as a component of $R_2$ is that it reacts specifically with the sample antibody to be detected. This molecule is preferably a binding partner according to the invention in a polymeric form which specifically binds the sample antibody. The binding partners in a polymeric form which are contained in $R_2$ are prepared by the same methods as the binding partners in a polymeric form for $R_1$.

A further component of the receptor $R_2$ is the label. A directly detectable substance is preferably used as a label for example a chemiluminescent, fluorescent or radioactive substance or a metal sol, latex or gold particle. Enzymes or other biological molecules are also preferred as the label such as for example haptens. Digoxigenin is a particularly preferred label among the haptens. Processes for labelling are familiar to a person skilled in the art and do not need to be elucidated further here. The label is detected directly in a well-known manner by measuring the chemiluminescent, fluorescent or radioactive substance or the metal sol, latex or gold particle or by measuring the substrate converted by the enzyme.

The label can also be detected indirectly. In this case a further receptor which itself is in turn coupled to a signal-generating group binds specifically to the label of $R_2$ such as a hapten like digoxigenin. The signal-generating group, for example a chemiluminescent, fluorescent or radioactive substance or an enzyme or gold particle, is detected by methods familiar to a person skilled in the art. An antibody or an antibody fragment can for example be used as the further receptor which binds specifically to the label of $R_2$. If this indirect detection of the label is used then the $R_2$ label is preferably digoxigenin or another hapten and the detection is carried out via an antibody coupled to peroxidase which is directed against digoxigenin or against the hapten.

In order to reduce interference by IgG antibodies of the same antigen specificity, binding partners in a monomeric form are added according to the invention to the test mixture. The term "monomer" means that the binding partners in a monomeric form according to the invention only contain one epitope region or only one binding site for the antibody whose interference is to be reduced i.e. a structure which immunologically reacts specifically with the IgG antibody. The monomeric structure of these binding partners is important in order to ensure that only the antigen-specific IgG antibodies whose interference is to be reduced bind to the binding partners in a monomeric form and not the IgM antibodies to be detected.

The epitope region can—as described above for binding partners in a polymeric form—for example be derived from an antigen or an anti-idiotype antibody. In accordance with the prerequisites for binding partners in a polymeric form, the epitope regions of binding partners in a monomeric form can also be derived from sugar and/or lipid structures or combined structures with peptide, lipid and/or sugar components. All structures that can be derived from an epitope region can be used which have a binding site to which the antibody of the IgG class whose interference is to be reduced specifically binds in the presence of IgM antibodies of the same specificity. The only prerequisite for the binding site i.e. for the binding partners used in monomeric form, is that the specific capability of binding to IgG is retained. This condition also applies to the case where sugar or lipid structures are present in the binding site.

According to the invention it is also possible to use binding partners in a monomeric form which flank or overlap the binding site to which the IgG antibody whose interference is to be eliminated specifically binds. Hence it is also possible to eliminate interference by IgG antibodies whose binding site includes an epitope which is not exactly identical with the epitope that is recognized by the IgM antibodies to be detected. These IgG antibodies can have a greater or lesser degree of cross-reactivity with the IgM antibodies to be detected. The addition of binding partners in a monomeric form which correspond to the epitopes of these cross-reacting antibodies and thus have a high affinity for these, also eliminates interference by these IgG antibodies. A mixture of binding partners in a monomeric form which overlap to a greater or lesser extent the epitopes of the IgM antibodies to be detected are preferably used to eliminate interference by IgG antibodies.

Peptides are preferably used as binding partners in a monomeric form. In the case of a protein as an analyte a binding site is understood—like the definition for the binding partner in a polymeric form—as a peptide, the sequence of which is part of the protein sequence of a protein antigen and to which an antibody directed towards this protein, which in the case of the present invention is an IgG antibody, specifically binds. In addition to these peptides a binding site is also understood to include peptides with amino acid sequences which have an essentially equivalent specificity and/or affinity of binding to the IgG antibody to be detected as the aforementioned peptides. These peptides can preferably be derived from the aforementioned peptides by substitution, deletion or insertion of individual amino acid residues.

Peptides according to the invention which correspond to a specific binding site are also understood to include peptide derivatives in which one or several amino acids have been derivatized by a chemical reaction. Examples of peptide derivatives according to the invention are in particular those molecules in which the backbone or/and reactive amino acid side groups, for example free amino groups, free carboxyl groups or/and free hydroxyl groups, have been derivatized. Specific examples of derivatives of amino groups are sulfonamides or carboxamides, thiourethane derivatives and ammonium salts for example hydrochlorides. Carboxyl group derivatives are salts, esters and amides. Examples of hydroxyl group derivatives are O-acyl or O-alkyl derivatives. The peptides are preferably produced by chemical synthesis according to methods known to a person skilled in the art and do not need to be especially elucidated here.

In addition the term peptide derivative also encompasses such peptides in which one or several amino acids are replaced by naturally occurring or non-naturally occurring amino acid homologues of the 20 "standard" amino acids. Examples of such homologues are 4-hydroxyproline, 5-hydroxylysine, 3-methylhistidine, homoserine, ornithine, β-alanine and 4-aminobutyric acid. The peptide derivatives must have an essentially equivalent specificity or/and affinity of binding to the IgG antibodies whose interference is to be reduced as the peptides from which they are derived.

Peptides according to the invention which correspond to a specific binding site are also referred to as peptide-mimetic substances named peptide-mimetics in the following which have an essentially equivalent specificity or/and affinity of binding to the IgG antibodies whose interference is to be reduced as the aforementioned peptides or peptide derivatives. Peptide-mimetics are compounds which can replace peptides with regard to their interaction with the antibody to be determined and can have a higher stability than the native peptides in particular towards proteinases and peptidases. Methods for the production of peptide-mimetics are described in Giannis and Kolter, "Angew. Chem." 105 (1993), 1303–1326 and Lee et al., Bull. Chem. Soc. Jpn. 66 (1993), 2006–2010.

The length of a binding site i.e. the length of a monomeric peptide according to the invention is usually at least 4 amino acids. The length is preferably between 4 and 20, 6 and 15 or particularly preferably 9 and 12 amino acids. In the case of peptide-mimetics or peptide derivatives an analogous length is necessary with regard to the size of the molecule.

The monomeric peptides according to the invention as a binding partner in a monomeric form contain the epitope to which the IgG antibody whose interference is to be reduced binds specifically. However, further flanking peptide sequences which no longer correspond to the specific epitope may be present at the N-terminal and/or at the C-terminal end of the peptide. This measure may be necessary to improve the solubility of the peptide. The only prerequisites are that the peptide as a binding partner in a monomeric form is actually present as a monomer and the ability to bind strongly to the IgG antibodies whose interference is to be reduced is retained.

A prerequisite for the use of the binding partners in a monomeric form (in this case: peptides) is that the same epitope is present in the monomeric form as that epitope which is present on the binding partners in a polymeric form or the polyhaptens in a polymeric form. This means that in order to effectively eliminate interference, the IgG antibodies which bind to the binding partners in a monomeric form, must have the same immunological specificity as the IgM antibodies to be detected. In an IgM antibody test interference should always be eliminated from IgG antibodies of the same antigen specificity.

The binding partners in a monomeric form are preferably used in a 10-fold to 10,000-fold excess compared to the concentration of the epitopes on the binding partners in a polymeric form. The binding partners in a monomeric form are preferably used in a 10-fold to 1000-fold and particularly preferably in a 100-fold excess. The concentration of the binding partners in a monomeric form is only limited insofar as the binding partners in a monomeric form are no longer soluble above a certain concentration. The concentration of the epitopes on the binding partners in a polymeric form depends on the size of the carrier material and can easily be individually determined by a person skilled in the art for any test procedure and any detection parameters. A guide value for the concentration of the epitopes on the binding partners in a polymeric form of 5 to 500 ng peptide per ml carrier material has proven to be suitable in the case of peptidic epitopes (length: 6 to 20 amino acids).

In addition to the binding partners in a monomeric form, additional interference-eliminating agents such as for example anti-Fd antibodies described in the introduction can also be used in order to additionally reduce interference by IgG antibodies.

Heterogeneous as well as homogeneous methods can be used as test procedures for the antigen-specific IgM test. In a homogeneous test procedure the complex composed of $R_1$, sample-IgM and $R_2$ is not bound to a solid phase. Instead the agglutination of several such complexes with one another leads to a turbidity which is a measure for the concentration of IgM. The binding partners in a monomeric form which reduce IgG interference do not inhibit the agglutination.

However, a heterogeneous method is preferably carried out. A method according to the bridge-test principle (see EP-A-0 280 211) is particularly preferably carried out. In one of the preferred embodiments a conjugate of a polyhapten according to the invention and a binding partner of a specific binding system, preferably biotin is used as $R_1$. $R_2$ is composed of a polyhapten according to the invention or binding partners in a polymeric form and a label, preferably digoxigenin. The same polyhaptens are particularly preferably used in $R_1$ and $R_2$. In this preferred embodiment the receptors $R_1$ and $R_2$ are incubated in the presence of the, in this case preferred, solid phase coated with avidin or streptavidin simultaneously with the sample and the binding partners in a monomeric form, preferably peptides. In this process the binding partners in a polymeric form of $R_1$ and $R_2$ react specifically with the IgM antibodies to be determined whereas the IgG antibodies of the same specificity are masked by the peptides i.e. by the binding partners in a monomeric form so that they cannot bind to the binding partners in a polymeric form. Thus the entire complex of avidin/streptavidin-$R_1$-IgM-sample antibody-$R_2$ is bound to the solid phase. After separating the solid phase from the liquid phase and optionally washing the solid phase, the complex bound to the solid phase is incubated with an additional receptor (in this case with an antibody directed against digoxigenin) which specifically recognizes the label of $R_2$. The further receptor is coupled to a signal-generating group preferably with the enzyme peroxidase. After a further optional washing step, the sample antibody is detected via the signal-generating group, in this case by the substrate converted by the enzyme. In this test procedure the incubation of the sample with $R_1$, $R_2$ the binding partners in a monomeric form and the additional receptor can also be carried out concurrently. This additionally simplifies the test procedure.

The test procedure described above is also very well suited for an application to automated systems. It is also possible to detect several antigen-specific IgM antibodies such as HIV antibodies against various HIV antigens. In such a case the additional receptor can also be used as a universal label since the additional receptor specifically recognizes the label of $R_2$. If several IgM antibodies with different antigen specificities are detected simultaneously, the polyhapten components of $R_1$ and $R_2$ as well as the binding partners in a monomeric form that are used to reduce interference must have the appropriate specificities.

All biological liquids known to a person skilled in the art can be used as samples. Body fluids such as whole blood, blood serum, blood plasma, urine, saliva etc. are preferably used as the sample.

In addition to the sample, the solid phase and the aforementioned receptors, other additives which may be required depending on the application such as buffer, salts, detergents, protein additives such as BSA may be present in the test mixtures. The necessary additives are known to a person skilled in the art or can be determined by him in a simple manner.

A subject matter of the invention is also a reagent for the determination of an antigen-specific antibody of the immunoglobulin M class which, in addition to the usual test additives for immunoassays, contains binding partners in a monomeric form i.e. preferably peptides and a receptor $R_1$ capable of binding to the antibody to be determined which is capable of binding to the solid phase and whose essential component is a binding partner in a polymeric form that is specifically recognized by the antibody to be determined.

A further subject matter of the invention is a reagent for the determination of an antigen-specific antibody of the immunoglobulin M class which, in addition to the usual test additives for immunoassays, contains binding partners in a monomeric form i.e. preferably peptides and two receptors $R_1$ and $R_2$ capable of binding to the antibody to be determined of which $R_1$ is capable of binding to a solid phase and $R_2$ carries a label wherein an essential component of each of the receptors $R_1$ and $R_2$ is a binding partner in a polymeric form that is specifically recognized by the antibody to be determined.

A further subject matter of the invention is the use of binding partners in a polymeric form for the antigen-specific determination of IgM antibodies by one of the aforementioned methods according to the invention.

An additional subject matter of the present invention is the use of binding partners in a monomeric form i.e. preferably peptides to reduce interference by IgG antibodies and/or rheumatoid factors in the determination of antigen-specific IgM antibodies.

The invention is elucidated by the following example.

EXAMPLE

Antigen-specific IgM Test: Anti-HIV 2-IgM

Biotin-labelled and digoxigenin-labelled multimeric antigens (HIV 2) are incubated with sample antibodies and a streptavidin-coated solid phase (incubation at 25° C. or 37° C., ca. 60 to 180 min, in this example: 120 min, 25° C.). After a wash step the immune complex bound to the wall reacts with an anti-digoxigenin-peroxidase conjugate (incubation at 25° C. or 37° C., ca. 30 to 120 min in this example: 60 min 25° C.). After a further wash step the peroxidase conjugate-labelled immune complex is detected by a substrate reaction (incubation at 25° C. or 37° C., for ca. 30 to 120 min, in this example: 60 min 25° C.).

The reaction steps (apart from the substrate reaction) take place in a Tris/HCl buffer (pH 7.5, 50 to 150 mM in this example 100 mM) containing ca. 0.05 to 0.4% detergent (here 0.2% polidocanol) and ca. 0.5% protein/protein derivative additives (here peptone from lactalbumin and BSA among others).

The sample antibodies in this case are monoclonal mouse antibodies (IgM and IgG) against a HIV2 epitope diluted to ca. 2–10 µg/ml in anti-HIV negative human serum.

The competition is carried out with a free unlabelled HIV 2 peptide antigen in a 10-fold or 100-fold excess compared to the concentration of the peptide epitopes on the polyhaptens.

Test signal in mA:

| Samples <HIV 2> MABs | Poly-haptens without free peptide | evaluation | poly-haptens plus free peptide 10-fold excess | evaluation | poly-haptens plus free peptide 100-fold excess | evaluation |
|---|---|---|---|---|---|---|
| IgM 2.6.6 | 2460 | pos. | 2488 | pos. | 2457 | pos. |
| IgM 2.22.8 | 1950 | pos. | 1990 | pos. | 1985 | pos. |
| IgG A | 2490 | pos. | 376 | borderline | 189 | neg. |
| IgG B | 626 | pos. | 167 | neg. | 152 | neg. |
| IgG C | 5699 | pos. test recognizes IgM and IgG | 1575 | pos. test recognizes IgM and a small amount of IgG | 286 | neg. test is IgM specific |

The addition of monomeric peptides makes the HIV 2 antibody test specific for IgM. Some samples give false-positive test results without the addition of peptide.

What is claimed is:

1. A method for the determination of an antigen-specific antibody of the immunoglobulin M class in a biological sample comprising an interfering antibody of the immunoglobulin G class having the same antigen specificity as said antibody of the M class, said method comprising the steps of:
   a. incubating said sample in a test mixture comprising:
      1) two different receptors, $R_1$ and $R_2$, wherein each of the said receptor binds specifically to said antibody of the M class, $R_1$ is bound directly or indirectly to a solid phase, $R_1$ is a binding partner in polymeric form, and $R_2$ carries a label, and
      2) a binding partner in a monomeric form that binds specifically to said antibody of the M class and to the antigen binding site of the antibody of the G class in an amount sufficient to reduce interference from said antibody of the G class,
   b. allowing a complex comprising $R_1$, said antibody of the M class, and labeled $R_2$ to form, and
   c. measuring said label bound by $R_2$ to said antibody of the M class as a measure of said antibody of the M class present in said sample.

2. The method of claim 1, wherein $R_2$ comprises a binding partner in polymeric form.

3. The method of claim 1, wherein $R_1$ is bound to said solid phase by a specific binding system selected from the group consisting of biotin/avidin, biotin/streptavidin, biotin/antibiotin, hapten/antihapten, Fc fragment of an antibody/antibody against said Fc fragment, and carbohydrate/lectin.

4. The method of claim 1, wherein said label is selected from the group consisting of chemiluminescent, fluorescent and radioactive substances, enzymes and biological molecules.

5. The method of claim 1, wherein said sample is simultaneously incubated with $R_1$ and $R_2$ and said binding partner in monomeric form.

6. The method of claim 1, wherein said test mixture also comprises an additional receptor which specifically binds to said label, wherein said additional receptor comprises a conjugate of a receptor specific for said label and a second label, wherein said second label is detennined as a measure of said antibody of the M class present in said sample.

7. The method of claim 1, wherein said binding partners in monomeric form are added in a 10-fold to 10,000-fold excess compared to the concentration of the epitopes on said receptors $R_1$ and $R_2$.

8. The method of claim 1, wherein said anitibody of the M class is an HIV 2 antibody.

* * * * *